(12) United States Patent
Bjorlin et al.

(10) Patent No.: US 7,933,781 B2
(45) Date of Patent: Apr. 26, 2011

(54) METHOD FOR REMOTELY MONITORING BIOLOGICAL DATA

(75) Inventors: Anders Bjorlin, Nynashamn (SE); Bjorn Soderberg, Akersberga (SE)

(73) Assignee: Kiwok Ltd., Nicosia (CY)

( * ) Notice: Subject to any disclaimer, the term of this patent is extended or adjusted under 35 U.S.C. 154(b) by 708 days.

(21) Appl. No.: 11/817,330

(22) PCT Filed: Feb. 9, 2007

(86) PCT No.: PCT/US2007/003592
§ 371 (c)(1),
(2), (4) Date: Aug. 29, 2007

(87) PCT Pub. No.: WO2007/095128
PCT Pub. Date: Aug. 23, 2007

(65) Prior Publication Data
US 2008/0189134 A1  Aug. 7, 2008

Related U.S. Application Data

(60) Provisional application No. 60/766,786, filed on Feb. 11, 2006.

(51) Int. Cl.
*G06Q 10/00* (2006.01)
*G06Q 50/00* (2006.01)

(52) U.S. Cl. .................................. 705/2; 705/3; 600/300
(58) Field of Classification Search .................. 705/2–3; 600/300
See application file for complete search history.

(56) References Cited

U.S. PATENT DOCUMENTS

| 6,336,900 | B1 | 1/2002 | Alleckson et al. |
| 2002/0026328 | A1* | 2/2002 | Westerkamp et al. ............ 705/2 |
| 2004/0152952 | A1* | 8/2004 | Gotlib et al. .................. 600/300 |
| 2005/0277872 | A1* | 12/2005 | Colby et al. .................... 604/67 |
| 2005/0278409 | A1* | 12/2005 | Kutzik et al. ................. 709/200 |

* cited by examiner

Primary Examiner — Luke Gilligan
(74) Attorney, Agent, or Firm — Fasth Law Offices; Rolf Fasth

(57) ABSTRACT

The method is for monitoring biological data in a human body. A sensor senses biological data from a human body and sends the biological data to a control unit that sends the biological data to a communicator. The communicator compares the biological data to triggering values. The communicator only transmits the biological data when the triggering values have been exceeded by the biological data. The communicator sends an alert signal including the biological data in a dedicated bandwidth to a server. A decision rule engine analyzes the biological data and decides which message to send and to which recipient based on the biological data. A medical institution pays a fee to a service unit for accessing the system.

7 Claims, 1 Drawing Sheet

METHOD FOR REMOTELY MONITORING BIOLOGICAL DATA

PRIOR APPLICATION

This application is a U.S. national phase application based on International Application No. PCT/US07/03592, filed 9 Feb. 2007, claiming priority from U.S. Provisional Patent Application No. 60/766,786, filed 11 Feb. 2006.

TECHNICAL FIELD

The method relates to a method for remotely monitoring biological data. More particularly, the monitoring is carried out by sensors mounted on a human body.

BACKGROUND OF INVENTION

There are many situations when it is important to monitor the health information of human subjects. It is often very inconvenient for patients to have to visit health institutions for routine check ups. For example, human subjects with a heart problem may require monitoring of the heart to identify possible heart problems before they actually occur. There is a need for an effective method for monitoring biological data and other information of users without requiring users/patients to visit the health institution each time.

SUMMARY OF INVENTION

The method of the present invention provides a solution to the above-outlined problems. More particularly, the method is for monitoring biological data in a human body. A sensor senses biological data from a human body and sends the biological data to a control unit that, in turn, sends the biological data to a communicator. The communicator compares the biological data to triggering values. The communicator only transmits the biological data when the triggering values have been exceeded by the biological data. The communicator sends an alert signal including the biological data in a dedicated bandwidth to a server. A decision rule engine analyzes the biological data and decides which message to send and to which recipient based on the biological data. A medical institution pays a fee to a service unit for accessing and using the system.

BRIEF DESCRIPTION OF DRAWING

The FIGURE is a schematic view of the system of the present invention.

DETAILED DESCRIPTION

Figure 1:
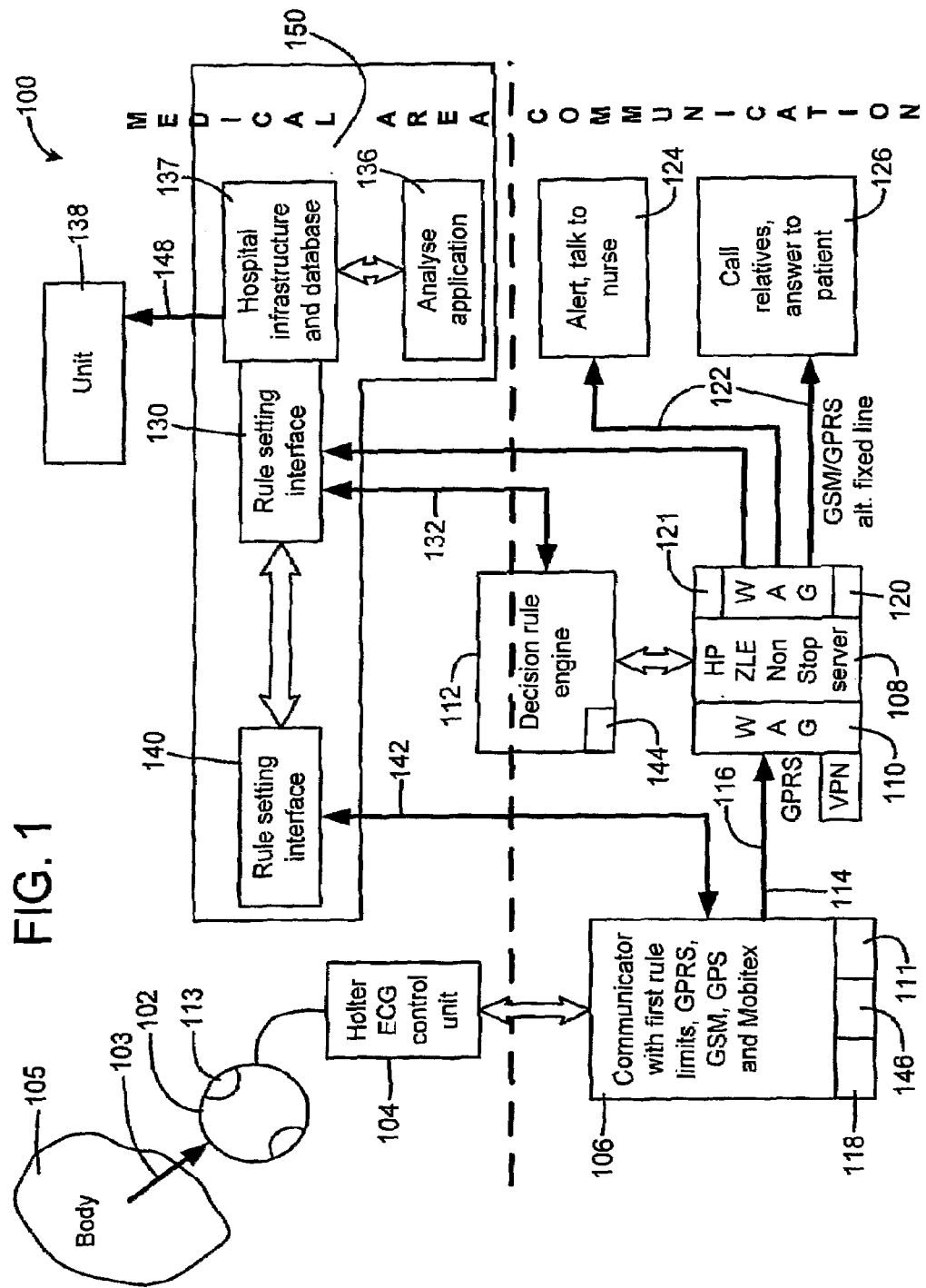

The FIGURE shows a system 100 that has a sensor 102. In general, the sensor 102 senses biological data 103 in biological signals from a human body 105. The sensor may include a plurality of standard electrodes that are mounted on the body 105 of the user/patient. The sensor may be electrically connected to a control unit 104 such as a Holter ECG control unit that measures the heart frequency. ECG apparatuses with one, two or any number of channels may be used. Of course, the sensor may measure and monitor a variety of biological data including, but not limited to, the blood pressure, oxygen level, blood sugar, and temperature.

The control unit 104 is in wireless communication with a communicator 106 such as a suitable PDA or another mobile communication device. The communication may be based on a suitable radio communication technology such as blue tooth technology or any other suitable technology.

The communicator 106 may be programmed with triggering values 111 that will trigger the communicator to transmit information. As discussed in detail below, the triggering values may have been put into the communicator 106 by authorized medical personnel or any other suitable person. Preferably, the communicator 106 should be programmed so that only authorized persons can obtain access to an update unit to change or update the triggering values 111. The suitable triggering values may also be stored in a central computer 137 at the doctor's office or hospital. For example, a rule-setting interface 140 may be used to communicate with the communicator 106 via signals 142. In this way, the triggering values 111 and other information in the communicator 106 may be modified remotely.

The communicator 106 is in communication with a real-time server 108, such as a non-stop server, that may have a wireless application gateway 110 that receives and sends information. For example, the communicator 106 may be using a dedicated bandwidth 116 of a mobile telephone network such as a VPN tunnel, as described below. The dedicated bandwidth makes communication easier to maintain without losing contact so that the communication channel there between is more reliable. By using the dedicated bandwidth 116, it is possible to develop a system that determines where a communication failure has occurred and the system can then continue sending the data communication when the communication failure has been repaired.

Preferably, the server 108 has an internal redundancy such as two hard-discs that are mirror images of one another so that basically no information is lost. Preferably, the gateway 110 should be designed to be able to automatically receive and transmit data communication in a wide variety of networks. The server 108 is in communication with a decision rule engine 112. The engine 112 is designed so that it knows where to automatically send or forward information upon receipt without having to save the information in a local database. For example, the engine 112 may decide whether information should automatically be forwarded directly to a physician as being urgent or just saved to be reviewed at a later date by a medical professional. An important feature is that the engine first determines the type of message it has received and then automatically forwards the information to the correct receiver or sends a new message to the correct receiver. In other words, the engine 112 may be pre-programmed with rules 144 to carry out certain steps depending upon the information it receives. The programming of which values to use for triggering signals may be based on established medical principles but also be based on the individual needs and unique profile of the patient. The programming of the engine 112 may be carried out by a rule setting interface 130 that are based on rules set out by a suitable medical professional. The engine 112 may also send a message back to the patient or relatives about what the patient should do. For example, the engine 112 may send a SMS to the patent with instructions. The setting of the engine 112 may be decided and set by the physician together with the patient via the rule-setting interface 130. In this way, the server is the central unit that handles the information flow from the sensors via the communicator and has the capacity of making decisions, storing and distributing information according to the rules as set out by the authorized personnel and possibly together with the patient. For example, the rule-setting interface 130 may send a signal 132 to modify the rules 144 of the engine 112. The server 108 may inform the interface 130 about available information by sending an alert signal 134. The information may be analyzed in an analysis unit 136.

When the triggering values 111 are exceeded by the data 113 of the biological data 103 of the biological signal sensed by the sensor 102, the communicator 106 sends an alert signal 114 to the server 108 via the dedicated bandwidth 116 that is particularly suited for data communication such as a VPN configured Internet access, as indicated above. The server 108 receives the signal 114 and may store identification information 118 of the communicator 106 and the incoming data 120 and sends an alert signal 122 to a health care unit 124 or to relatives 126 that there is information to be obtained.

Location information 146 of the communicator (106) may be stored in the server 108. The position of the communicator 106 may be updated on a regular basis such as every hour. Preferably, the location information 146 of the communicator 106 may also be saved at the same time as the data 120 is saved.

The system includes a communication service unit 138 so that the user or medical institution (150) pays a fee 148 for having access to the service. The fee may be a flat rate or be based on the number of transactions.

While the present invention has been described in accordance with preferred compositions and embodiments, it is to be understood that certain substitutions and alterations may be made thereto without departing from the spirit and scope of the following claims.

The invention claimed is:

1. A method for monitoring biological data in a human body, comprising:
   providing a system having a sensor in communication with a control unit that is in communication with a mobile telecommunication device, the mobile telecommunication device being in communication with a real-time server that is in communication with a decision rule engine;
   the sensor sensing biological data from a human body, the sensor sending the biological data directly to a control unit;
   the control unit sending the biological data to the mobile telecommunication device;
   the mobile telecommunication device receiving the biological data and comparing the biological data to triggering values;
   the mobile telecommunication device transmitting the biological data when the triggering values have been exceeded by the biological data;
   the mobile telecommunication device sending an alert signal including the biological data in a dedicated bandwidth to the real-time server;
   the real-time server directly receiving the biological data from the mobile telecommunication device and sending the biological data directly from the real-time server to the decision rule engine;
   the decision rule engine receiving the biological data directly from the real-time server and analyzing the biological data and deciding which message to send and to which recipient based on the biological data and preprogrammed rules; and
   the decision rule engine automatically sending the biological data to a medical professional without first saving the biological data in a database.

2. The method according to claim 1 wherein the method further comprises a rule setting interface setting the triggering values of the mobile telecommunication device.

3. The method according to claim 1 wherein the method further comprises the mobile telecommunication device communicating with the server via a VPN tunnel.

4. The method according to claim 1 wherein the method further comprises putting the server in communication with a medical professional.

5. The method according to claim 1 wherein the method further comprises the engine sending a message back to the mobile telecommunication device with instructions that are based on information in the alert signal received from the mobile telecommunication device.

6. The method according to claim 1 wherein the method further comprises a rule setting interface sending a signal to the engine to modify preprogrammed rules of the engine.

7. The method according to claim 1 wherein the method further comprises providing the alert signal with location information of the mobile telecommunication device.

* * * * *